United States Patent [19]
Yamaguchi

[11] Patent Number: 4,747,412
[45] Date of Patent: May 31, 1988

[54] ELECTRONIC SPHYGMOMANOMETER WITH GRAPHICAL OUTPUT
[75] Inventor: Keiji Yamaguchi, Shimizu, Japan
[73] Assignee: Terumo Kabushiki Kaisha, Tokyo, Japan
[21] Appl. No.: 883,367
[22] Filed: Jul. 8, 1986
[30] Foreign Application Priority Data Jul. 9, 1985 [JP] Japan .................................. 60-149132
Jul. 9, 1985 [JP] Japan .................................. 60-149133

[51] Int. Cl.⁴ .............................................. A61B 5/02
[52] U.S. Cl. ................................... 128/683; 128/680; 128/682; 346/33 ME
[58] Field of Search ............................... 128/677–683, 128/670–672, DIG. 900; 340/722, 753–754; 364/415, 417; 346/33 ME

[56] References Cited
U.S. PATENT DOCUMENTS

| | | | |
|---|---|---|---|
| 3,996,928 | 12/1976 | Marx | 128/683 X |
| 4,228,506 | 6/1981 | Ripley et al. | |
| 4,484,584 | 11/1984 | Uemura | 128/680 |
| 4,517,986 | 5/1985 | Bilgutoy | 128/683 X |
| 4,592,364 | 6/1986 | Pinto | 128/672 |
| 4,608,994 | 9/1986 | Ozawa et al. | 128/670 |

OTHER PUBLICATIONS

*Wescon Tech. Papers,* vol. 19, Sep. 16–19, 1975, Session 20, Article 5, pp. 1–10, Singer et al., "Outpatient Monitoring With Portable Microprocessor Recording System".
*Proceeding of the Fall Joint Computer Conference,* Nov. 17–19, 1970, pp. 609–614, Sacks et al., "Concurrently Statistical Evaluation During Patient Monitoring".
Hewlett-Packard Journal, vol. 13, No. 11, Nov. 1980, pp. 3–11, Blancke et al., "Patient Monitoring Enhanced by New Central Station".
Hodley, H. R. et al., "Experience with a Simplified Computer–Based IC Monitory System", 3rd Am. Symp. on Comp. Appl. in Med. Oct. 14–17, 1979, Wash. D.C., pp. 348–357.
Geddes, L. A. "Measurement of Blood Pressure", Yrbk Publ., Chicago 1970, p. 112.

*Primary Examiner*—Francis J. Jaworski
*Attorney, Agent, or Firm*—Staas & Halsey

[57] ABSTRACT

A sphygmomanometer measures blood pressure inclusive of systolic and diastolic blood pressure values, pulse rate and atmospheric temperature prevailing at the time of measurement. The sphygmomanometer includes a memory for storing plural sets of information relating to measured blood pressure together with time information relating to the times at which the measurements were taken, and a printer for generating a graph having a time axis and an axis for information relating to blood pressure. In a first output mode, the printer graphically records systolic and diastolic blood pressure values that prevailed at the time of measurement, connects these two values with a line segment and graphically records pulse rate and atmospheric temperature that prevailed at the time of measurement on the time axis together with the corresponding systolic and diastolic blood pressure values. In a second output mode, the printer numerically records systolic and diastolic blood pressure values, date and time of measurement, pulse rate and atmospheric temperature and in addition produces a graph pattern of reference blood pressure regions with axes of systolic and diastolic blood pressure and with the measured blood pressure indicated thereon.

10 Claims, 14 Drawing Sheets

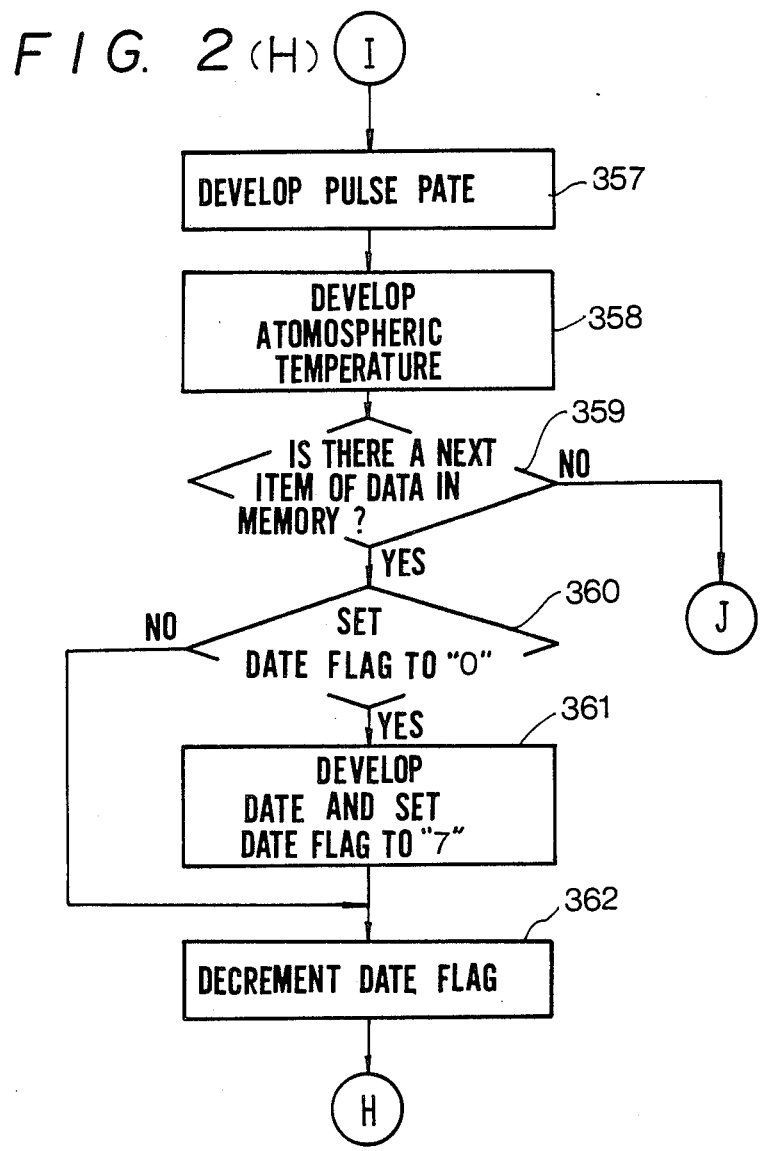

FIG. 3 (A)

| 31 | | | | | 33 |
|---|---|---|---|---|---|
| 1 | 2 | 3 | 4 | ∼ | 30 |
| ▨ | ▨ | | | | |
| 1 | 0 | 0 | 0 | ∼ | 0 |

FIG. 3 (B)

| 31 | | | | | 33 |
|---|---|---|---|---|---|
| 1 | 2 | 3 | 4 | ∼ | 30 |
| ▨ | ▨ | Clear | ▨ | | ▨ |
| 0 | 0 | 1 | 0 | ∼ | 0 |

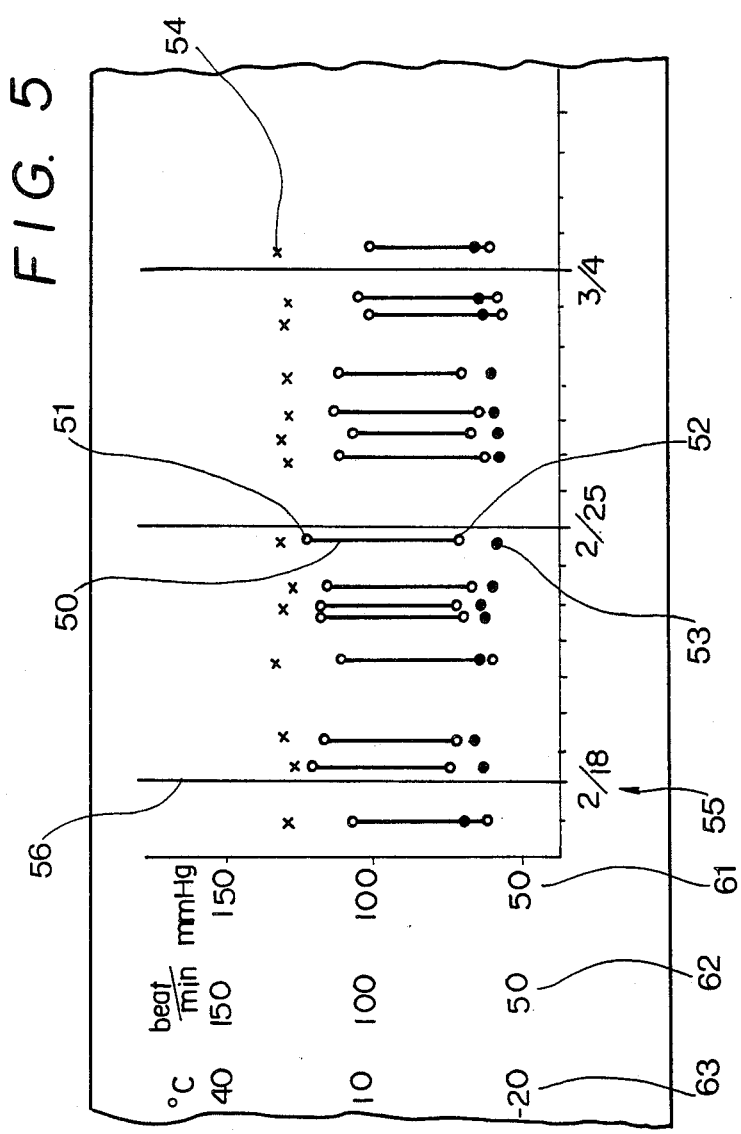

ELECTRONIC SPHYGMOMANOMETER WITH GRAPHICAL OUTPUT

BACKGROUND OF THE INVENTION

This invention relates to an electronic sphygmomanometer having recording means for producing a hard copy of measured blood pressure.

In a conventional electronic sphygmomanometer, measured blood pressure is displayed or recorded by a liquid-crystal display unit or recording means such as a printer each time a measurement is completed. However, merely displaying or recording the numerical values of systolic and diastolic blood pressure on a measurement-by-measurement basis does not enable one to fully comprehend the variation which these values undergo. More specifically, blood pressure is a constantly varying quantity by nature and one cannot tell from a mere single measured value thereof whether that value is an ordinary blood pressure for the individual. Moreover, since blood pressure varies depending upon the individual's mental and physical state and the external surroundings at the time of measurement, one cannot tell from the results of only a single measurement whether the individual's blood pressure is truly abnormal. Accordingly, in order to correctly grasp the meaning of a measured value of blood pressure, it is important to accumulate the results of measurements taken a number of times every several hours or every other day and observe the variation in these blood pressure values.

Thus, observing the change in blood pressure values is vital in terms of controlling an individual's blood pressure. For this reason, the written operating instructions provided with electronic sphygmomanometers are almost always accompanied by special recording note paper for the purpose of recording measured blood pressure values. However, writing down the results of each and every measurement is a very troublesome task so that the user eventually tires of the task of continuously writing down the measured values. It is doubtful whether correct diagnosis of the patient's condition can be made in such a situation.

Temperature, humidity and the temperature-humidity index are some of the environmental factors that are intimately related to changes in blood pressure. Among these factors, temperature is especially critical. In general, the lower the atmospheric temperature, the higher blood pressure tends to become. However, temperature and other environmental information that has an influence on blood pressure cannot be measured and recorded with the conventional electronic sphygmomanometers.

In other electronic sphygmomanometers, all that is done is to provide a numerical display of a measured blood pressure value on a liquid-crystal display unit or a printed indication of the measured value by means of a printer at the completion of each measurement. In consequence, measured values of systolic and diastolic blood pressure cannot be compared with an appropriate blood pressure to enable the relationship between them to be readily understood. The state of the art is such that the relationship can only be understood after first being subjected to processing.

SUMMARY OF THE INVENTION

An object of the present invention is to provide an electronic sphygmomanometer which solves the aforementioned problems encountered in the prior art.

Another object of the present invention is to provide an electronic sphygmomanometer capable of recording the results of a large number of blood pressure measurements and of recording and displaying a trend in blood pressure variation in a time series in the form of a single graph.

According to the present invention, the foregoing objects of the invention can be attained by providing an electronic sphygmomanometer comprising: measuring means for measuring information related to blood pressure inclusive of at least systolic and diastolic blood pressure values; timekeeping means for clocking times at which measurement is performed by the measuring means; memory means for storing plural sets of systolic and diastolic blood pressure values measured by the measuring means together with the times clocked by the timekeeping means when measurements of the blood pressure values are taken; pattern holding means for holding a graph pattern having a first axis along which time is plotted and a second axis along which measured systolic and diastolic blood pressures are plotted; reading means for reading times and measured values out of the memory means in a time series; blood pressure developing means for developing systolic and diastolic blood pressure values among the measured values read out by the reading means as positions on the graph pattern on the basis of the clocked times; line segment developing means for developing line segments connecting the systolic and diastolic blood pressure values in each set thereof developed by the blood pressure developing means, each line segment forming a bar graph pattern; printing means for printing out the bar graph patterns developed by the line segment developing means; and control means for transmitting developed data from each of the developing means to the printing means, and for causing the printing means to print out the developed data.

According to a preferred embodiment of the invention, the measuring means is provided with pulse rate measuring means for measuring a patient's pulse rate, and with pulse rate developing means for developing the measured pulse rate on the first axis of the graph pattern at a point in time identical with that at which a corresponding set of systolic and diastolic blood pressure values is indicated on the graph pattern, the control means causing the printing means to print out the pulse rate on the graph pattern.

According to another preferred embodiment of the invention, the measuring means is provided with atmospheric temperature measuring means for measuring atmospheric temperature when blood pressure is measured, and with atmospheric temperature developing means for developing the measured atmospheric temperature on the first axis of the graph pattern at a point in time identical with that at which a corresponding set of systolic and diastolic blood pressure values is indicated on the graph pattern, the control means causing the printing means to print out the atmospheric temperature on the graph pattern.

According to an embodiment of the invention, time information is indicated at predetermined intervals along the first axis, each item of time information serving as a guide when the graph pattern is read.

According to an embodiment of the invention, a partitioning pattern is indicated on the graph pattern at predetermined time intervals for dividing the graph pattern into the time intervals.

Still another object of the present invention is to provide an electronic sphygmomanometer capable of indicating measured values of pressure on a graph on which an appropriate blood pressure region has been superposed, thereby enabling the relationship between the measured blood pressure values and the appropriate blood pressure values to be readily ascertained.

According to the present invention, the foregoing objects are also attained by providing an electronic sphygmomanometer comprising: measuring means for measuring information related to blood pressure inclusive of at least systolic and diastolic blood pressure values; memory means for storing the information measured by the measuring means; pattern holding means for holding a graph pattern having a first axis along which systolic blood pressure is plotted and a second axis along which diastolic blood pressure is plotted, a reference blood pressure region for blood pressure diagnosis being indicated on the graph pattern; calculating means for calculating, based on the systolic and diastolic blood pressure values measured by the measuring means, a point of intersection indicating the systolic and diastolic blood pressure values on the graph pattern held by the pattern holding means; developing means for developing the point of intersection calculated by the calculating means as data on the graph pattern; printing means for recording on recording means the developed data resulting from the development performed by the developing means; and control means for controlling transmission of the developed data from the developing means to the printing means; whereby the measured systolic and diastolic blood pressure values are indicated and recorded as the point of intersection on the graph pattern and the reference blood pressure region is indicated and recorded in a form superposed on the point of intersection.

According to a preferred embodiment of the present invention, the measuring means is provided with atmospheric temperature measuring means for measuring atmospheric temperature when blood pressure is measured. The control means sends information indicative of the measured atmospheric temperature recorded by the recording means to the printing means together with the developed data from the developing means, whereby the printing means is capable of recording the measured atmospheric temperature.

Further, the measuring means is provided with means for measuring a patient's pulse rate when blood pressure is measured. The control means sends the measured pulse rate recorded by the recording means to the printing means together with the developed data from the developing means, whereby the printing means is capable of recording the measured pulse rate.

In an embodiment of the invention, the reference blood pressure region for blood pressure diagnosis is demarcated by boundary lines indicating respective boundaries of the region.

Further, the reference blood pressure region for blood pressure diagnosis includes a high-blood pressure area, a marginal blood pressure area and a normal blood pressure area. The high-blood pressure area covers systolic blood pressure values above 160 mmHg and diastolic blood pressure values above 95 mmHg, the marginal blood pressure region covers systolic blood pressure values ranging from 140 mmHg to 160 mmHg and diastolic blood pressure values ranging from 90 mmHg to 94 mmHg, and the normal blood pressure area covers systolic blood pressure values no higher than 139 mmHg and diastolic blood pressure values no higher than 89 mmHg.

Still another object of the present invention is to provide an electronic sphygmomanometer capable of being selectively set to one of two function modes.

According to the present invention, the foregoing object is attained by provided an electronic sphygmomanometer having:

selecting means for selectively setting the electronic sphygmomanometer to one of first and second function modes, the electronic sphygmomanometer comprising the following;

when set to the first function mode:

measuring means for measuring information related to blood pressure inclusive of at least systolic and diastolic blood pressure values; timekeeping means for clocking times at which measurement is performed by the measuring means; memory means for storing plural sets of measured values measured by the measuring means together with the times clocked by the timekeeping means when the measurements are taken; pattern holding means for holding a graph pattern having a first axis along which time is plotted and a second axis along which measured systolic and diastolic blood pressures are plotted; reading means for reading times and measured values out of the memory means in a time series; blood pressure developing means for developing systolic and diastolic blood pressure values among the measured values read out by the reading means as positions on the graph pattern on the basis of the clocked times; line segment developing means for developing line segments connecting the systolic and diastolic blood pressure values in each set thereof developed by the blood pressure developing means, each line segment forming a bar graph pattern; printing means for printing out the bar graph patterns developed by the line segment developing means; and control means for transmitting developed data from each of the developing means to the printing means, and for causing the printing means to print out the developed data;

when set to the second function mode:

measuring means for measuring information related to blood pressure inclusive of at least systolic and diastolic blood pressure values; memory means for storing the information measured by the measuring means; pattern holding means for holding a graph pattern having a first axis along which systolic blood pressure is plotted and a second axis along which diastolic blood pressure is plotted, a reference blood pressure region for blood pressure diagnosis being indicated on the graph pattern; calculating means for calculating, based on the systolic and diastolic blood pressure values measured by the measuring means, a point of intersection indicating the systolic and diastolic blood pressure values on the graph pattern held by the pattern holding means; developing means for developing the point of intersection calculated by the calculating means as data on the graph pattern; printing means for recording on recording means the developed data resulting from the development performed by the developing means; and control means for controlling transmission of the developed data from the developing means to the printing means; whereby the measured systolic and diastolic blood pressure values are indicated and recorded as the point of intersection on the graph pattern and the reference blood pressure region is indicated and recorded in a form superposed on the point of intersection.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

FIGS. 3(A) and 3(B) are views showing the manner in which the results of measurement are stored in memory;

FIG. 5 is a view illustrating an example of a printout of measurement results stored in memory in accordance with an embodiment of the invention.

DESCRIPTION OF THE PREFERRED EMBODIMENT

A preferred embodiment of the present invention will now be described in detail with reference to the drawings.

Figure 1:
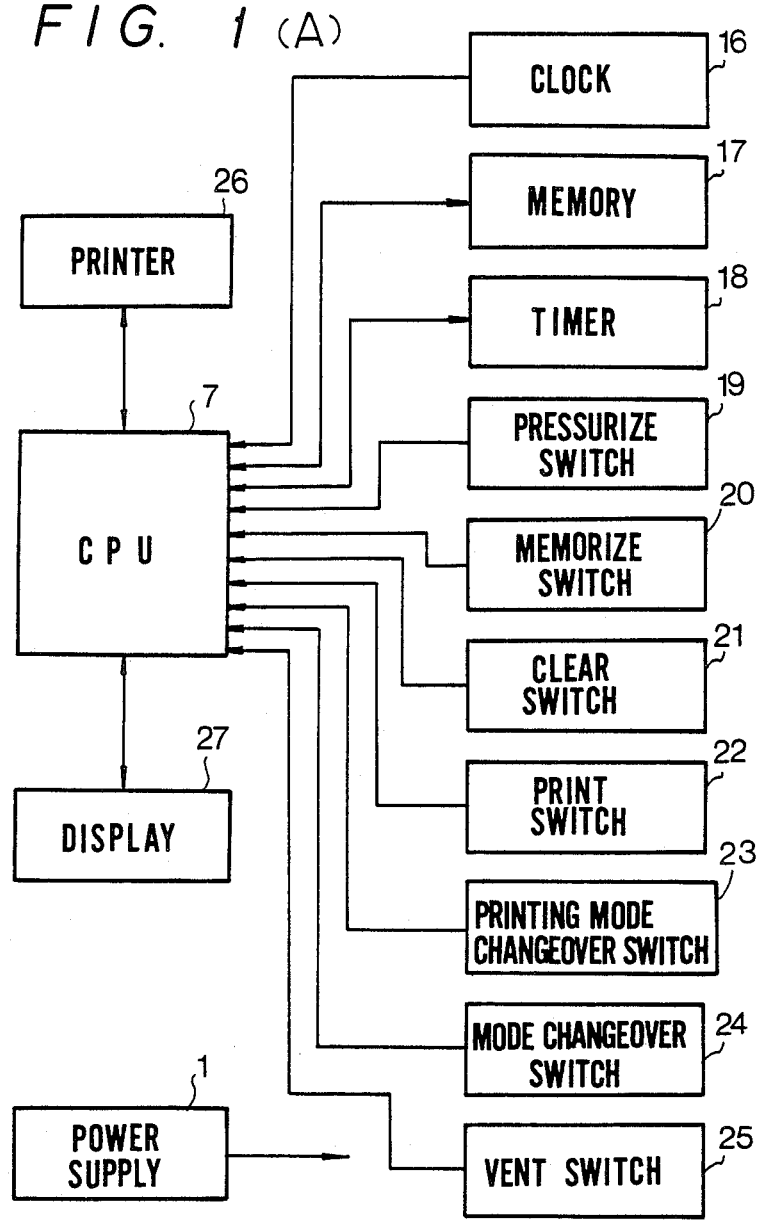
FIGS. 1(A) and 1(B) are block diagrams illustrating a preferred embodiment of an electronic sphygmomanometer according to the present invention.
Figure 1:
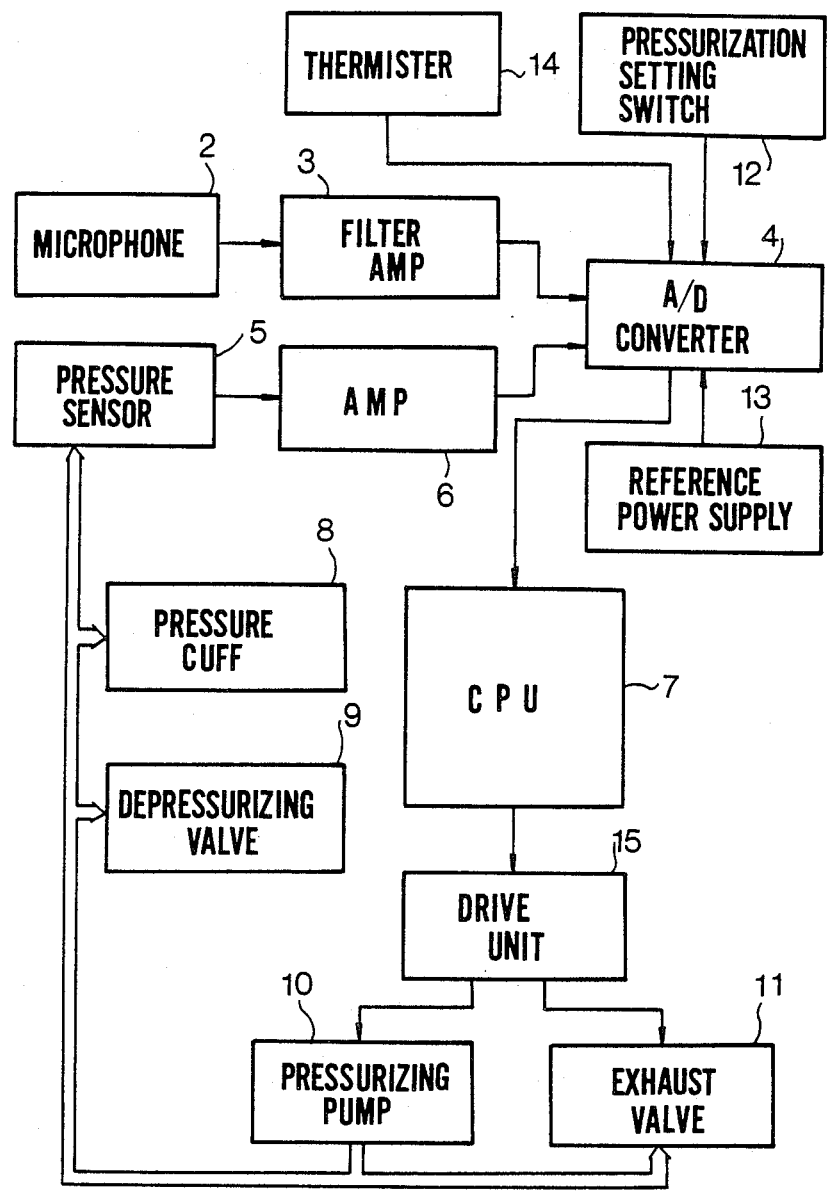

FIGS. 1(A) and 1(B) are block diagrams illustrating an embodiment of an electronic sphygmomanometer according to the present invention. The electronic sphygmomanometer includes a power supply 1 for supplying the various components of the instrument with electric power, a microphone 2 for detecting sounds and/or vibration produced by a blood vessel in a limb of a patient to which a pressure cuff 8 is affixed, a filter amplifier 3 for wave-shaping and amplifying an output signal produced by the microphone 2, an analog/digital (A/D) converter 4 for converting analog signals from the filter amplifier 3 and an amplifier 6 into digital signals, a pressure sensor 5 for sensing pressure within the cuff 8 and for converting the sensed pressure into an electric signal outputted as a pressure information signal, the amplifier 6 for amplifying the pressure information signal from the pressure sensor 5, and a control unit (a central processing unit, hereafter referred to as a "CPU") 7 for executing overall control of the electronic sphygmomanometer in accordance with a program, described below, stored in an internal read-only memory (ROM).

Connected to the pressure cuff 8 are a depressurizing valve 9 for reducing the pressure of air inflating the cuff, a pressurizing pump 10 for inflating the cuff 8 with air under the control of the CPU 7, and an exhaust valve 11 for venting air from cuff 8 under the control of the CPU 7. A pressurization setting switch 12 is connected to the A/D converter 4 for setting a pressure value to which the cuff 8 is to be inflated by the pressurizing pump 10. A reference power source 13 gererates a reference voltage applied to the A/D converter 4 for use thereby. A thermister 14 is connected to the A/D converter 4 for measuring ambient temperature at the time of a blood pressure measurement. Connected between the CPU 7 and the pressurizing pump 10 and exhaust valve 11 is a drive unit 15 for controlling the pump 10 and valve 11 in response to commands from the CPU 7.

Also connected to the CPU 7 are a clock 16 for generating a clock signal which decides the operation timing of the CPU 7, a memory 17 for storing the results of measurement such as measured values of blood temperature, a timer 18 having a timekeeping function, and switches 19–5 for controlling the operation of the electronic sphygmomanometer according to the illustrated embodiment.

The abovementioned switches 19 - 25 connected to the CPU 7 include a pressurize switch 19 which instructs the CPU 7 to initiate pressurization of the cuff 8 as well as measurement of blood pressure, a memorize switch 20 which instructs the CPU 7 to store measured values in the memory 17 and to display the measured value on a display unit 27, described below, a clear switch 21 which instructs the CPU 7 to erase the contents of the memory 17, a print switch 22 which instructs the CPU 7 to print out via a printer 26, described below, the results of measurement stored in the memory 17, a printing mode changeover switch 23 which instructs the CPU 7 to changeover the printing mode of the printer 26, a sphygmomanometer/clock mode changeover switch 24 which instructs the CPU 7 to place the electronic sphygmomanometer of the illustrated embodiment in a blood pressure measurement mode or a timekeeping mode, in which the results of clocking the signal from the clock 16 are displayed on the display unit 27, and a vent switch 25 which instructs the CPU 7 to forcibly vent air from the cuff 8 by means of the exhaust valve 11. The details of the processing executed by the CPU 7 in response to inputs from the above switches will be described below.

The printer 26 is for printing out the results of measurements and constitutes printing means in cooperation with the CPU 7 and switches 20 through 23. The display unit 27 is for displaying the results of measurements and is equipped with a buzzer, not shown.

The operation of the electronic sphygmomanometer of the illustrated embodiment having the above construction will now be described.

When the sphygmomanometer/clock mode changeover switch 24 has been set to the clock mode, the CPU 7 performs a timekeeping operation based on the clock signal from the clock 16 and displays time on the display unit 27 in a well-known manner. In other words, when the switch 24 is set as described, the electronic sphygmomanometer of the present embodiment functions as a electronic clock. The timekeeping processing in the clock mode is performed continuously even during the execution of processing in the electronic sphygmomanometer mode, described below. When the mode changeover switch 24 has been set to the clock mode, the electronic sphygmomanometer starts operating in the clock mode and the results of timekeeping are immediately displayed on the display unit 27.

Let us now refer to the flowcharts of FIGS. 2(A) to 2(D) to describe control for a case where the mode changeover switch is set to the electronic sphygmomanometer mode.

When the mode changeover switch 24 is set to the electronic sphygmomanometer mode, the program proceeds to a step 100, at which processing for electronic measurement of blood pressure is executed. Specifically, a step 110 calls for an initial setting operation, at which the pressure sensor 5 is subjected to a zero-point adjustment, the voltage of the power supply 1 is checked, and the like. If the power supply voltage is improper, the buzzer with which the display unit 27 is provided is sounded and a suitable message is made to appear on the display unit 27. Note that if a battery is used as the power supply 1, the improper supply voltage mentioned above will occur when the battery discharges to such an extent that the supply voltage drops below a stipulated value.

When the initial settings have been made, the program proceeds to a step 111, at which the CPU 7 reads in atmospheric temperature information. More specifically, the thermister 14, which is attached to the surface of the sphygmomanometer, senses atmospheric temperature and produces an analog output signal indicative thereof. The analog output of the thermister 14 is applied to the A/D converter 4 directly or, if necessary, following amplification by an amplifier, in order to be converted into a digital signal. The temperature in the form of this digital signal is read in by the CPU 7. Next, at a step 112, the read temperature information is converted into degrees Fahrenheit (°F.) or centrigrade (°C.) by the CPU 7 and is displayed on the display unit 27. This is followed by a step 120, at which the CPU 7 determines whether the memory switch 20 is in the ON position. If the decision is NO, the program proceeds to a step 130, at which the CPU determines whether the pressurize switch 19 is in the ON position. In other words, the CPU 7 waits for inputs from the switches 20, 19 at the steps 120, 130, respectively. If the CPU 7 receives an input from the pressurize switch 19 at the step 130, the program proceeds to a step 140, which calls for the CPU 7 to read in the pressurization value to which the pressurization setting switch 12 has been set. Next, at a step 150, a measured value memory unit (not shown) incorporated in the CPU 7 is cleared of the results of an immediately preceding measurement (blood pressure value, pulse rate, atmospheric temperature, date and time of measurement). An internal record flag in the CPU 7 is reset to "0" at a step 151 [FIG.2(B)]. Next, at a step 152, the atmospheric temperature is measured by the thermister 14, just as in the step 111 described above, and the measured temperature is stored in the measured value memory unit in the CPU 7.

The program then proceeds to a step 160, where the drive unit 15 is actuated to close the exhaust valve 11 and place the pressurizing pump 10 in operation. Next, at step 170, the pressure in the cuff 8 is measured by the pressure sensor 5 and the CPU 7 waits for the set pressurization value to be reached. If, at a step 175, the CPU 7 receives an input from the vent switch 25 in the course of pressurization, the program proceeds to a step 176, at which the CPU 7 actuates the drive unit 15 to open the exhaust valve 11, thereby forcibly venting the air from the cuff 8. The program then proceeds to a step 230 [FIG. 2(C)].

The CPU 7 is constantly reading in the pressure signal from the pressure sensor 5 during pressurization and depressurization. If the CPU 7 determines at the step 170 that the pressure in cuff 8 has reached the set pressurization value in the course of pressurization, the program proceeds to a step 180, at which the operation of the pressurizing pump 10 is halted. Following halting of pump 10, the depressurizing valve 9 begins depressurizing the cuff 8 by allowing a small amount of air to leak from the cuff at a constant rate. Measurement starts at a step 190. Measurement of systolic blood pressure, diastolic blood pressure and pulse rate are performed in a well-known manner based on blood vessel sounds and Korotkoff sounds picked up by the microphone 2.

When measurement of systolic blood pressure, diastolic blood pressure and pulse rate are completed, the measured values are stored in the measured value memory unit in CPU 7 at a step 200. This is followed by a step 210 [FIG. 2(C)], at which the drive unit 15 is actuated to open the exhaust valve 11, whereby compulsory venting of the air from the cuff 8 is started. Each of the measured values is then displayed on the display unit 27 at a step 220.

Figure 2:
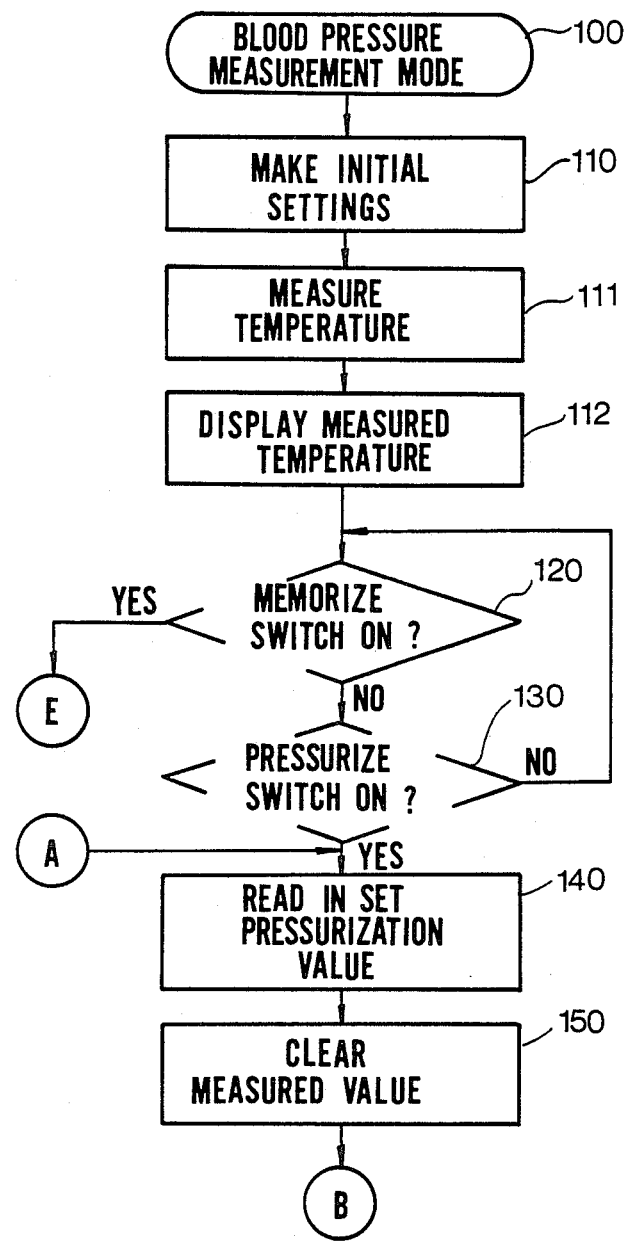
FIGS. 2(A) to 2(I) are flowcharts illustrating a control operation in accordance with the embodiment of the invention.
Figure 2:
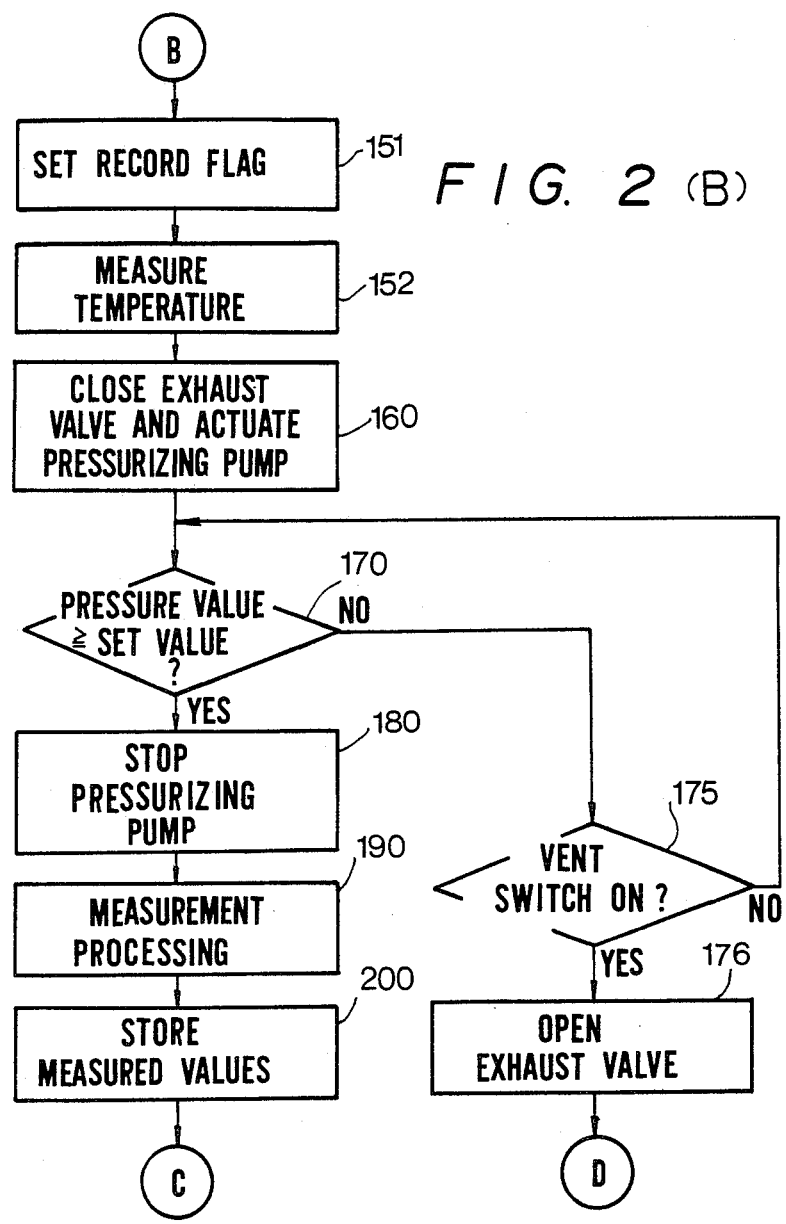
Figure 2C:
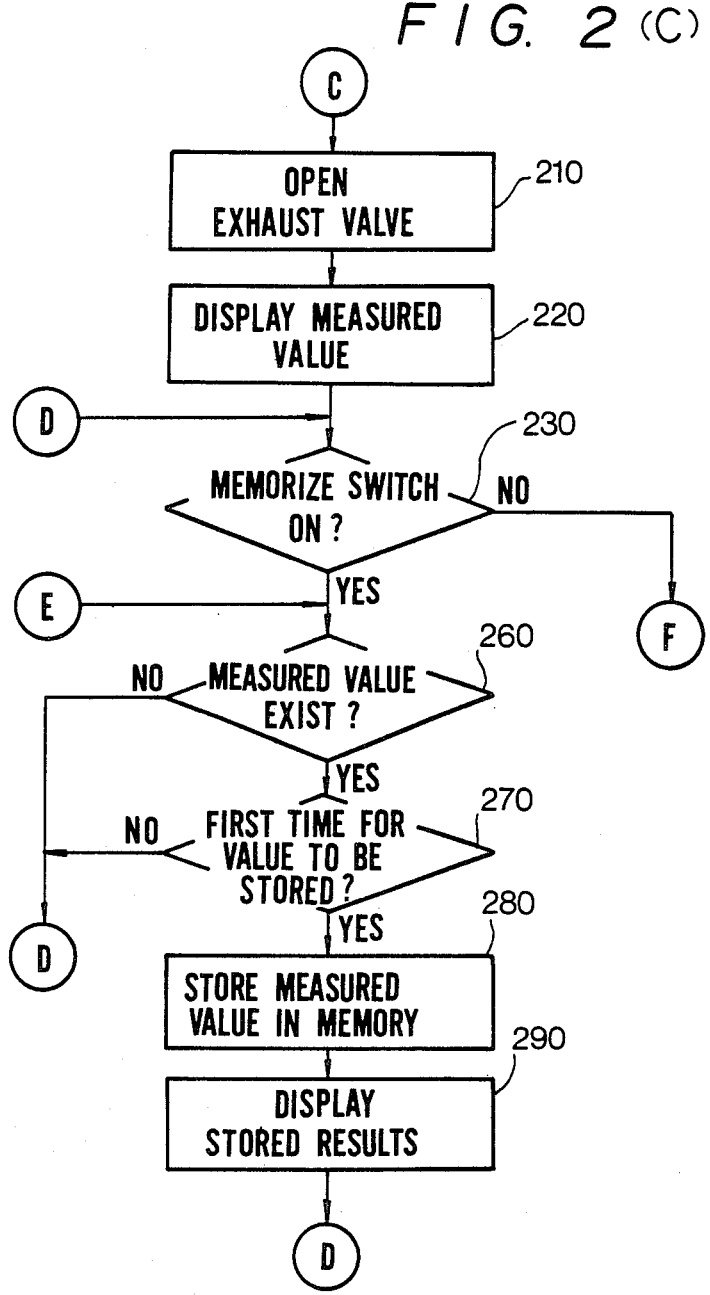
Figure 2:
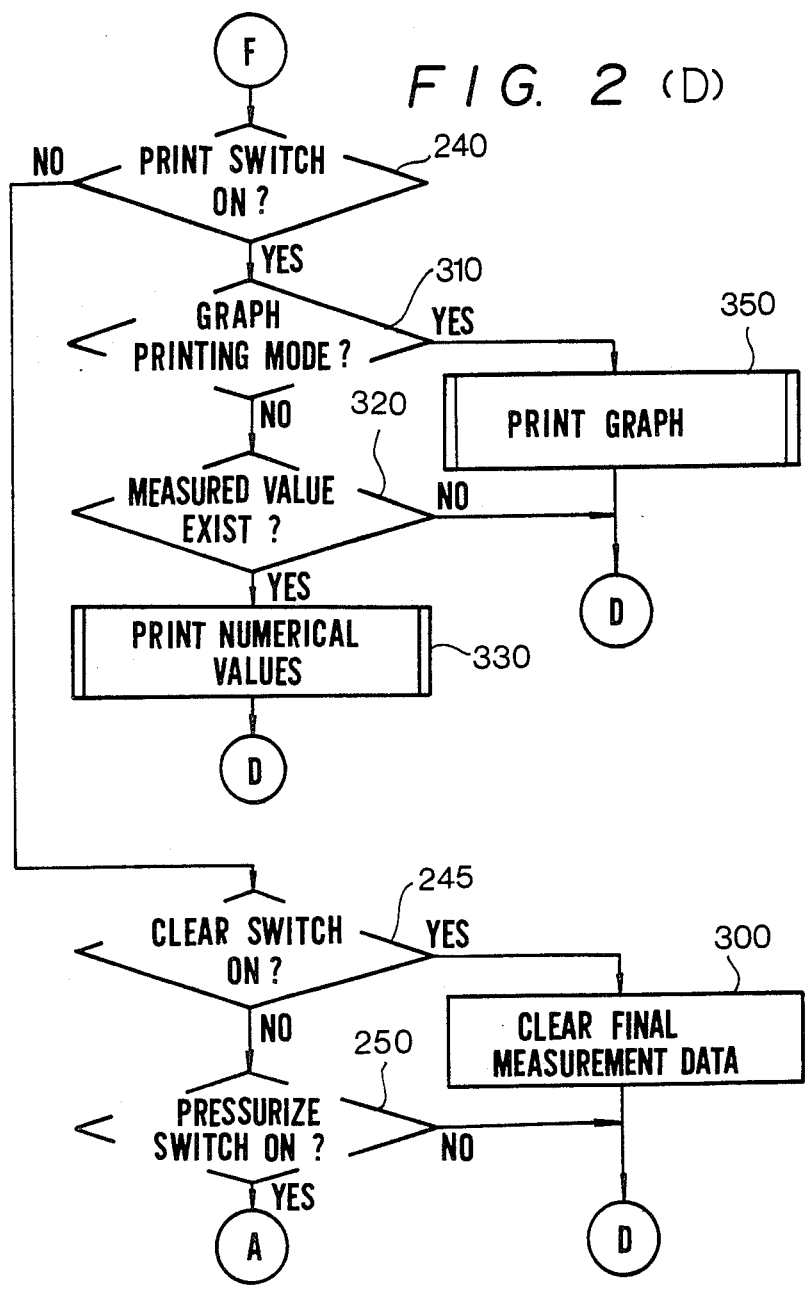

This is followed by steps 230, 240 [FIG. 2(D)], 245 and 250, at which the CPU 7 waits for an input from the memorize switch 20, print switch 22, clear switch 21 or pressurize switch 19, respectively. Accordingly, the measured values continue to be displayed on the display unit 27 while the CPU 7 waits.

If the CPU receives an input from the pressurize switch 19 at the step 250, then the program returns to the step 140 and measurement begins. If the CPU 7 receives an input from the memorize switch 20 at the step 230 [FIG. 2(C)], the program proceeds to a step 260 to begin processing for the storage of measured values in the memory 17. Note that this step is also executed when an input is received from the memorize switch 20 at the step 120.

The step 260 calls for the CPU 7 to confirm that measured values have been stored in its stored value memory unit. Since the memory unit has been cleared, the program returns directly to the step 230. If measured values have been stored in the memory unit of the CPU 7, the program proceeds to a step 270, at which it is determined whether this is the first time the memorize switch 20 has been operated following a measurement. Since the record flag is "0", a YES answer is obtained at the step 270. If the record flag is "1", indicating that the memorize switch 20 has been operated two or more times, the program returns directly to the step 230 and operation of the memorize switch 20 is invalidated. The reason for this is to prevent the results of a single measurement from being stored in the memory 17 repeatedly.

When it is determined at the step 270 that the record flag is "0", namely that this is the first operation of the memorize switch 20, the measured values in the memory unit of the CPU 7 are stored in the memory 17 at a step 280.

The memory 17 has 30 segments, each of which stores data concerning blood pressure obtained by a single measurement. The information includes the atmospheric temperature, systolic and diastolic blood pressure values, pulse rate and the time and date of the measurement. If such data are stored in the memory 17 thirty or less, the data are stored in order starting from segment 1. In such a case a pointer is provided for designating the starting segment.

The manner in which the data are stored in the memory 17 is illustrated in FIG. 3(A). Numeral 31 denotes the segment numbers, 32 data storage areas for storing the measurement data, and 33 a pointer area. If data have been stored in memory 17 thirty times or less, the lead data storage area having logical "1" set in the pointer area 33 will be segment 1, as shown in FIG. 3(A). For example, if measurement data have been stored up to segment 2 of the data storage areas 32, as indicated by the shaded portions in FIG. 3(A), then the next measurement data will be stored in segment 3 and the pointer area 33 remains unchanged. When 31 or more storage operations take place, the data in the lead data storage area are cleared and the latest measurement data are written into this storage area. In other words, assume that logical "1" has been set in the pointer area 33 of segment 3. In order to store new measurement data in segment 3 of data storage area 32, segment 3 of this storage area, the pointer area 33 of which has been set to "1", is first cleared, as shown in FIG. 3(B). This is followed by writing the new measurement data into this storage area. After the new measurement data have been written, the pointer area 33 of segment 3 is reset to logical "0" and the pointer area 33 of segment 4 is set to logical "1". Accordingly, segment 4 will be updated the next time measurement data are stored in memory 17.

When measurement data have thus been stored in the memory 17, the program proceeds to a step 290, at which the record flag is set to "1" and the display unit 27 presents a display informing of the fact that the storage of the measurement data in memory 17 has ended. (Alternatively, the buzzer can be sounded to indicate that the data have been stared.) The program then returns to the step 230.

If the CPU 7 receives an input from the clear switch 21 at the step 245, the next step executed is a step 300, at which the measurement data stored last in the memory 17 are erased. If data have been stored in every segment of memory 17, the data in the data storage area 32 whose pointer area 33 has been set to "1" will be erased.

If the CPU 7 receives an input from the print switch 22 at the step 240, the program proceeds to a step 310 to start processing, described below, for the printing of measurement results by the printer 26. The printer 26 is of the dot matrix type and is capable of printing any pattern.

At the step 310, which is the first step of the print processing, the CPU 7 determines whether the printing mode changeover switch 23 has been set to a graph printing mode or a numerical value printing mode. If the switch has been set to the numerical value printing mode, the program proceeds from the step 310 to a step 320, at which the CPU 7 determines whether measurement data have been stored in its measured value memory unit. If no measurement data are present, the input from the print switch 22 is invalidated and the program returns to the step 230. If measurement data do exist in the memory unit, the CPU 7 executes a numerical value printing subroutine at a step 330 before the program returns to the step 230. The details of this subroutine will be described below with reference to the flowchart of FIGS. 2(E) and 2(F).

The following items are capable of being printed and outputted as numerical values in the numerical value printing subroutine, i.e. in the numerical value printing mode: data provided by the timekeeping means indicative of the date and time of measurement; as well as atmospheric temperature, systolic and diastolic blood pressure values and pulse rate, which are stored in the measured value memory unit of CPU 7. In addition, a graph is generated in which diastolic blood pressure values are plotted along the vertical axis and systolic blood pressure values are plotted along the horizontal axis, and the measured values of blood pressure are indicated on the graph.

Figure 2E:
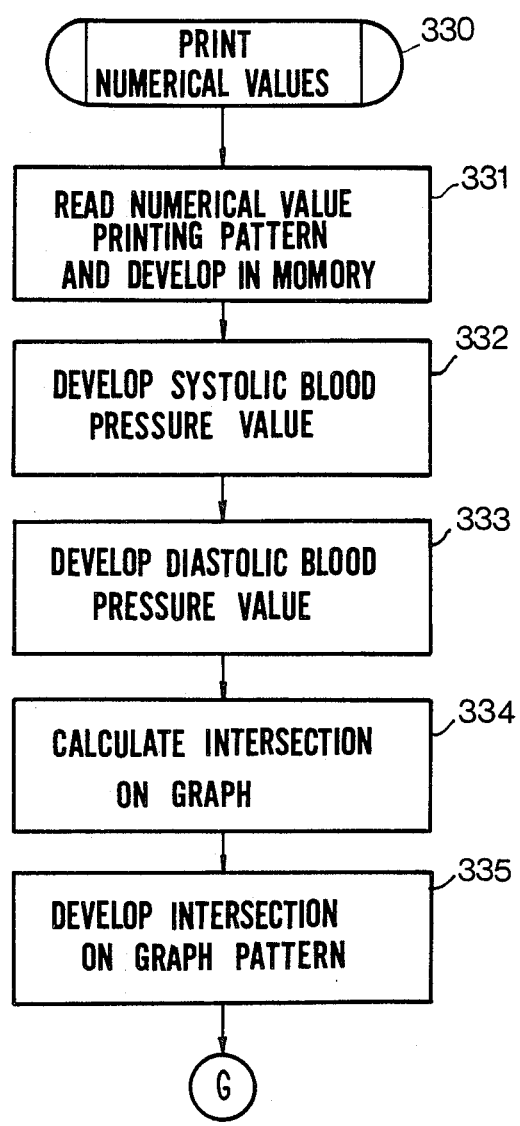
Figure 2:
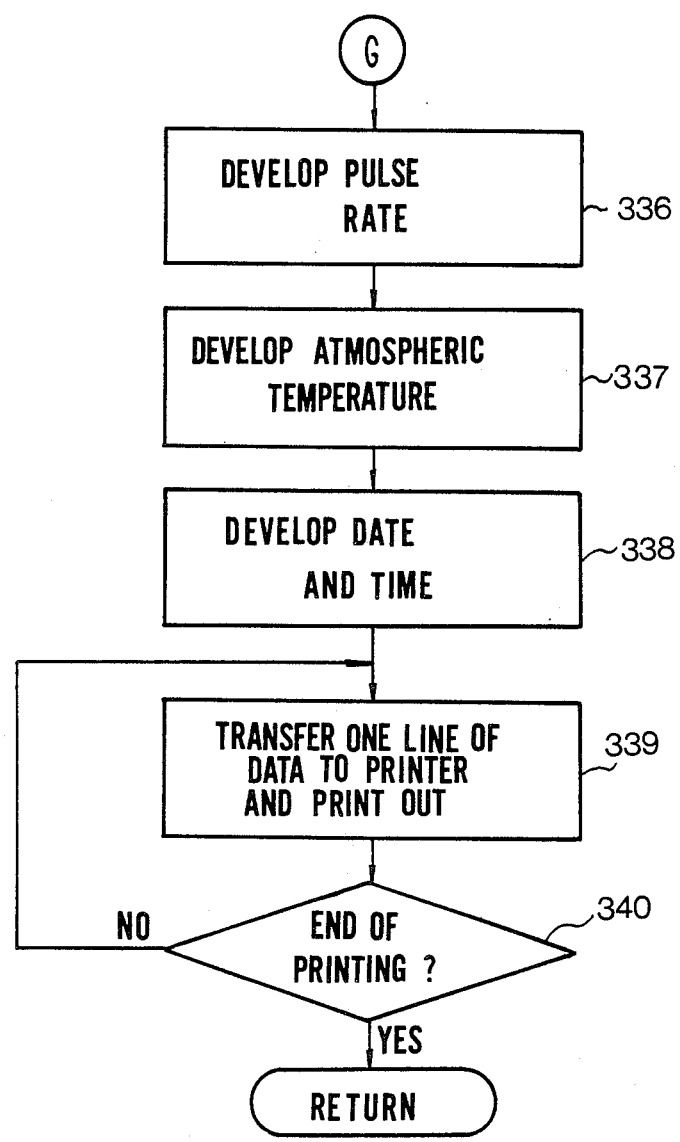
Figure 2:
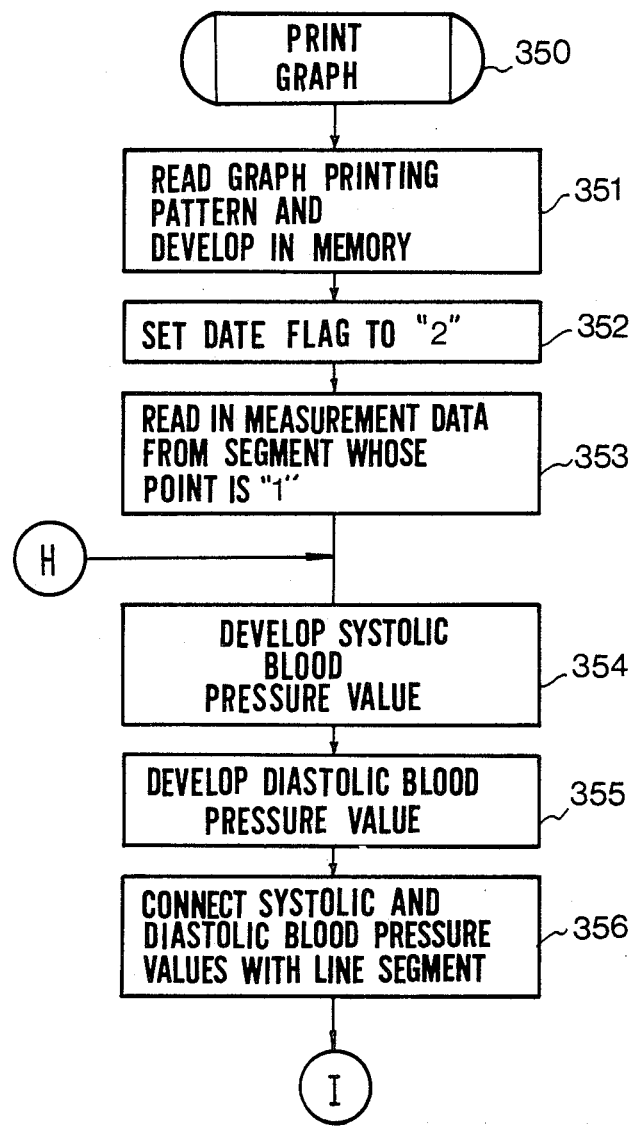
Figure 2:
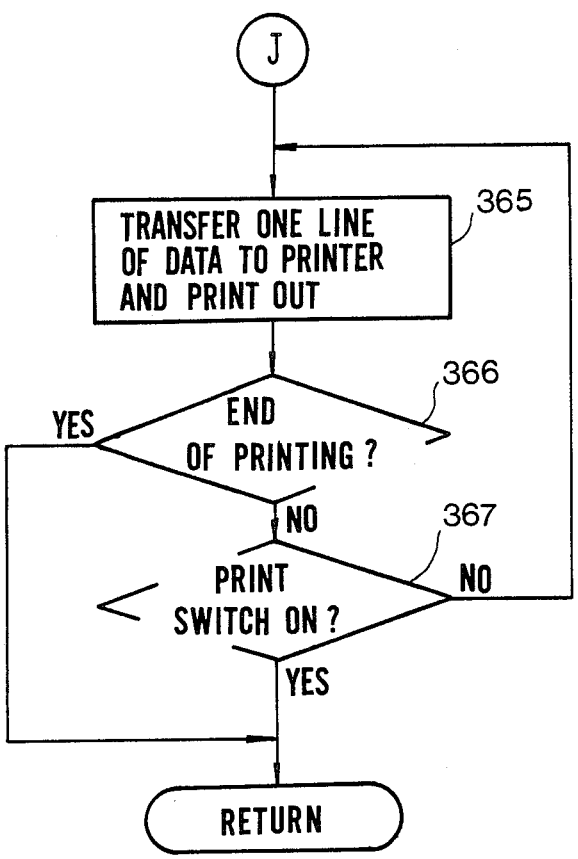

As shown in FIG. 2(E), the first step of the numerical value printing subroutine is a step 331, at which a numerical value printing pattern stored in a ROM in CPU 7 is read out of the ROM and stored (developed) in a printing buffer area of the memory 17.

Figure 4:
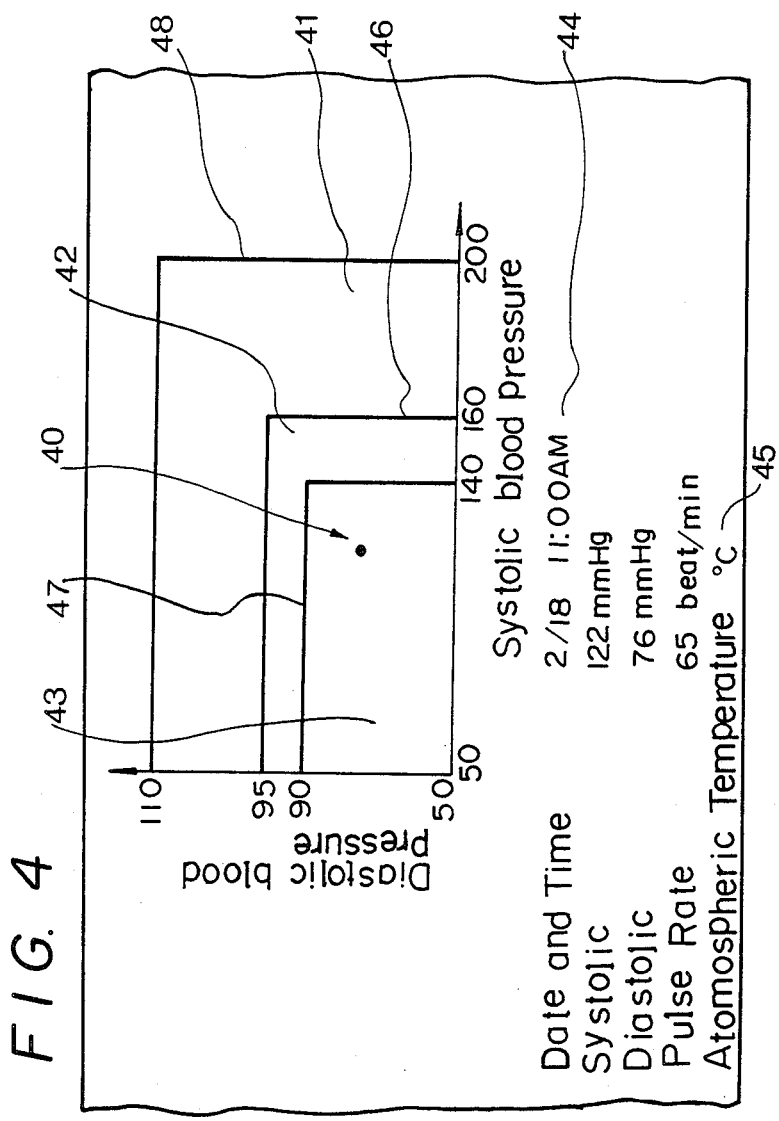
FIG. 4 is a view illustrating an example of a print-out of measurement results according to an embodiment of the invention.

As shown in FIG. 4, the numerical value printing pattern is a graph pattern having the diastolic blood pressure values along its vertical axis and the systolic blood pressure values along its horizontal axis. A point indicating measured systolic and diastolic blood pressure values, as shown at 40 in FIG. 4, the date and time of measurement, indicated at 44, and values of measured blood pressure, pulse rate and atmospheric temperature, shown at 45, do not form part of the pattern. The graph pattern does include a reference blood pressure region for blood pressure diagnosis. This region indicates where the measured values of systolic and diastolic blood pressure are located with respect to a proper blood pressure.

The reference blood pressure region is divided into several areas. These are a high-blood pressure area 41 on the outside of a high-blood pressure boundary line 46 indicating systolic blood pressure values above 160 mmHg and diastolic blood pressure values above 95 mmHg, a marginal high-blood pressure area 42, which is located on between the high-blood pressure boundary line 46 and the proper blood pressure boundary line 47, indicating systolic blood pressure values ranging from 140 mmHg to 160 mmHg and diastolic blood pressure values ranging from 90 mmHg to 94 mmHg, and a normal blood pressure area 43 on the inner side of the proper blood pressure boundary line 47 indicating systolic blood pressure values no higher than 139 mmHg and diastolic blood pressure values no higher than 89 mmHg. Numeral 48 denotes a boundary line indicating a region which requires to be monitored at all times.

It should be noted that instead of reading these patterns out of the ROM in CPU 7, they can be stored in the memory 17 and read out of this memory when printing is performed. The processing for generating these patterns is the same as that executed in the graph printing mode, described below.

When development of the graph pattern is completed in the manner set forth above, the program proceeds to a step 332, at which the systolic blood pressure value is developed in a numerical value printing region (45 in FIG. 4) of the printing buffer area. Next, at a step 333, the diastolic blood pressure value is developed in a similar manner, and a point of intersection 40 (FIG. 4) between the systolic and diastolic blood pressure values is obtained on the graph at a step 334. This is followed by a step 335, at which the point of intersection is developed in a graph area of the printing buffer area. Next, the program proceeds to a step 336 [FIG. 2(F)], at which the pulse rate is developed in the numerical value printing region 45, then to a step 337, at which the atmospheric temperature is developed in the numerical value printing region 45, and then to a step 338, at which the date and time of measurement are developed in a date and time area (44 in FIG. 4).

All data to be printed out are thus developed as patterns in the printing buffer area of memory 17. At the completion of this processing, the program proceeds to a step 339, at which printing image data are transferred line by line to the printer 26 to be printed out by a well-known method. When all of the printing data in the printing buffer area have been printed out, which is confirmed at a step 340, the processing of the present subroutine is ended and a return is effected to the main program. It should be noted that the measurement data, which are stored in digital form, are converted into the corresponding printing image data by a well-known character generator or the like. In accordance with the illustrated embodiment, the variety of characters which need to be generated by conversion are very few.

If the graph printing mode is selected at the step 310 in FIG. 2(D), graph printing processing is executed at step 350. The measurement data stored in memory 17 are printed out in order starting from the segment whose pointer has been set to "1".

In accordance with the graph printing processing, the measurement data stored in memory 17 are printed out on a graph successively in a time series. The blood pressure values are plotted along the vertical axis and the measurement times are plotted along the horizontal axis.

The flowchart of FIGS. 2(G), 2(H) and 2(I) illustrates the graph printing subroutine executed in the graph printing mode. The first step of the subroutine is a step 351, at which a graph printing pattern is read out of the ROM in CPU 7 and developed in the printing buffer area of memory 17. As shown in FIG. 5, the graph printing pattern is a graph pattern exclusive of the results of measurement. The graph has a vertical axis along which blood pressure values are plotted. Indicated to the left of the blood pressure values are pulse rates in terms of beats per minute (beat/min) and atmospheric temperatures in terms of degrees Centigrade (°C.). Along the vertical axis, numeral 61 denotes the blood pressure values, 62 the pulse rate values and numeral 63 the atmospheric temperature values. The horizontal axis of the graph is a time axis exclusive of the date.

When the graph printing pattern has been developed in the printing buffer area, the program proceeds to a step 352, at which a date flag (not shown) in memory 17 is set to "2". Next, at a step 353, measurement data are read out of the data storage area 32 of memory 17 whose pointer 33 has been set to "1". In the event that the pointer 33 has not been set to "1", the measurement data are read out of the data storage area 32 of segment 1. This is followed by a step 354, at which the CPU 7 finds the position on the graph corresponding to the systolic blood pressure value among the measurement data read out at the step 353. A small white circle, shown at 51 in FIG. 5, is developed at this position. Next, at a step 355, the diastolic blood pressure is similarly developed at a small white circle indicated at 52 in FIG. 5. The circles at 51, 52 are connected by a line segment at a step 356, thus producing a bar graph indicated at 50 in FIG. 5. Accordingly, the arrangement is such that systolic and diastolic blood pressure values which prevail at the moment of measurement can be recognized at glance. Next, pulse rate is developed at a position marked by a small black circle, as shown at 53 in FIG. 5, at a step 357 [FIG. 2(H)], and the atmospheric temperature at the time of measurement is developed at a position marked by an X, as shown at 54 in FIG. 5, at a step 358. This is followed by a step 359, at which the CPU 7 determines whether a succeeding item of print data is stored in the data storage area of memory 17. If measurement data to be printed out still remain in this data storage area, then the program proceeds to a step 360, where it is determined whether the date flag is "0". If the answer is NO, the program proceeds to a step 362; if YES, then the next step executed is a step 361, at which a printing pattern representing the date of the read measurement data is developed at a predetermined position along the horizontal (time) axis of the graph.

The printing pattern includes not only a numeric pattern indicating the date, shown at 55, but also a boundary pattern 56 provided at predetermined intervals along the time axis to serve as a guide or partitioning when the graph is read. When pattern development ends, a date flag is set to "7" at the step 361, after which the program proceeds to the step 362, where the date flag is decremented by 1 before the program returns to the step 354. Here processing begins for developing the read measurement data in the printing buffer area.

If it is found at the step 359 that all of the measurement data stored in memory 17 have been developed in the printing buffer area, the program proceeds to a step 365 [FIG. 2(I)], at which one line of printing image data stored in the printing buffer area are transmitted to the printer 26. The data transmitted are printed out by the printer 26 on recording paper in a manner well-known in the art. Next, a step 366 calls for a determination as to whether all of the printing data in the printing buffer have been printed out. If the answer is YES, processing of this subroutine is ended and a return is effected to the main program. If the answer is NO at the step 366, the program proceeds to a step 367, at which the CPU 7 checks whether an input is arriving from the print switch 22. The reason for this is that the print switch 22 may be pressed again during a print-cut, in which case printing processing is interrupted to return to the step 230 at the moment this occurs. If it is determined at the step 367 that an input has arrived from the print switch 22, the program immediately returns. If there is no input from the switch 22, the program returns to the step 365 in order that the next line of data may be printed out.

As mentioned earlier, blood pressure varies constantly and one cannot tell from a single measured value thereof whether that value is an ordinary blood pressure for the individual. Accordingly, in order to correctly grasp the meaning of a measured value of blood pressure, it is important to accumulate the results of measurements taken a number of times every several hours or every other day and observe the variation in these blood pressure values. Blood pressure values undergo a subtle change depending upon an individual's psychological state and tend to rise temporarily when the individual is placed under stress. Consequently, the act of measuring a patient's blood pressure may itself cause his blood pressure to rise, as when the measurement is taken by a doctor or amongst a large group of people. When such is the case, what the patient's blood pressure would be under ordinary conditions cannot be accurately determined, with the risk that medication for lowering blood pressure may be prescribed for a patient who merely becomes tense easily. This could cause the patient harm. Measured blood pressure values also fluctuate depending upon ambient temperature at the time of measurement. By measuring blood pressure over an extended period of time and indicating the measured values simultaneously, as shown in FIG. 5 in accordance with an embodiment of the invention, the variation in blood pressure values can be accurately grasped with ease, thus enabling a proper diagnosis to be made.

The present invention has the following advantages.

(1) By being provided with recording and memory functions, the electronic sphygmomanometer of the invention makes it possible for a temporal change in blood pressure to be outputted automatically in the form of a graphical representation.

(2) By being provided with a clear switch, the electronic sphygmomanometer of the invention enables the operator to erase erroneously stored data.

(3) By being provided with a memorize switch, the electronic sphygmomanometer of the invention enables the operator to judge whether the results of measurement are correct (an incorrect measurement can be caused by noise) or whether the results are data rendered unnecessary for some other reason. Accordingly, the electronic sphygmomanometer can be made to memorize trend data correctly.

(4) By being provided with a printing mode changeover function, the electronic sphygmomanometer of the invention is capable of providing a hard copy of blood pressure values obtained at each and every measurement.

(5) By being providing with a mode (clock/sphygmomanometer) changeover function, the electronic sphygmomanometer of the invention can be used as a clock and, at the same time, enables the operator to verify the operation of an internal clock (timer) at a glance.

(6) Since atmospheric temperature is measured and displayed at the time of a measurement, any variation in blood pressure caused by environmental conditions can be ascertained.

According to the invention, the manner in which systolic and diastolic values of blood pressure measured over an extended period of time vary can be indicated on a graph. This enables the variation to be recognized at a glance.

Thus, according to the present invention as described above, systolic and diastolic values of measured blood pressure can be indicated as a point of intersection on a graph, so that the state of the measured blood pressure values can be recognized at a glance. In addition, a proper blood pressure region is superposed on the graph so that the significance of the measured blood pressure values can be readily understood.

Since the atmospheric temperature and the patient's pulse rate at the time of a blood pressure measurement are measured and indicated according to an embodiment of the invention, a variation in blood pressure caused by the environment can also be understood.

According to an embodiment of the invention, the patient's pulse rate is indicated on a graph along with the blood pressure values. This permits both the patient's average blood pressure and psychological state at the time of measurement to be grasped simultaneously. Since the atmospheric temperature at the time of blood pressure measurement is also measured and indicated on the graph, a variation in blood pressure ascribable to the patient's surroundings can be grasped as well.

As many apparently widely different embodiments of the present invention can be made without departing from the spirit and scope thereof, it is to be understood that the invention is not limited to the specific embodiments thereof except as defined in the appended claims.

What we claim is:

1. An electronic sphygmomanometer comprising:
   measuring means for measuring information related to blood pressure at a plurality of times, the information including at least systolic and diastolic blood pressure values;
   pattern holding means for holding a graph pattern having a first axis along which systolic blood pressure is plotted and a second axis along which diastolic blood pressure is plotted, and for holding a reference blood pressure pattern for blood pressure diagnosis for superposition on the graph pattern;
   calculating means for calculating, based on the systolic and diastolic blood pressure values measured by said measuring means, a point of intersection indicating the systolic and diastolic blood pressure values on the graph pattern held by said pattern holding means;
   developing means for developing the point of intersection calculated by said calculating means as data on the graph pattern;
   printing means for recording on recording media the graph pattern, the reference blood pressure pattern and the developed data resulting from the developing performed by said developing means; and
   control means for controlling transmission of the graph and reference patterns from said pattern holding means and the data developed by said developing means to said printing means, whereby the systolic and diastolic blood pressure values are indicated and recorded as the point of intersection on the graph pattern and the reference blood pressure pattern is indicated and recorded in a form superposed on the point of intersection.

2. An electronic sphygmomanometer according to claim 1, wherein said measuring means includes atmospheric temperature measuring means for measuring the value of atmospheric temperature when blood pressure is measured, and said control means being further for sending the value of the measured atmospheric temperature recorded by said recording means to said printing means together with the developed data from said developing means, whereby said printing means is capable of recording the value of the measured atmospheric temperature.

3. An elelctronic sphygmomanometer according to claim 1,
   wherein said measuring means includes means for measuring the value of a pulse rate when the blood pressure is measured, and
   wherein said control means is further for sending the value of the pulse rate, included in the information related to blood pressure, to said printing means together with the data developed by said developing means, whereby said printing means is capable of recording the value of the pulse rate.

4. An electronic sphygmomanometer according to claim 1, wherein the reference blood pressure pattern for blood pressure diagnosis comprises boundary lines indicating respective regions of blood pressure.

5. An electronic sphygmomanometer according to claim 4, wherein the boundary lines of said reference blood pressure pattern for blood pressure diagnosis serve to define a high-blood pressure area, a marginal blood pressure area and a normal blood pressure area.

6. An electronic sphygmomanometer according to claim 5 wherein the high-blood pressure area covers systolic blood pressure values above 160 mmHg and diastolic blood pressure values above 95 mmHg, the marginal blood pressure area covers systolic blood pressure values ranging from 140 mmHg to 160 mmHg and diastolic blood pressure values ranging from 90 mmHg to 94 mmHg, and the normal blood pressure area covers systolic blood pressure values no higher than 139 mmHg and diastolic blood pressure values no higher than 89 mmHg.

7. An electronic sphygmomanometer comprising:

selecting means for selectively setting said electronic sphygmomanometer to one of first and second function modes;

measuring means for measuring information related to blood pressure inclusive of at least systolic and diastolic blood pressure values;

timekeeping means for clocking times at which measurements are performed by said measuring means;

memory means for storing plural sets of the information measured by said measuring means together with the times clocked by said timekeeping means when the measurements were taken;

first pattern holding means for holding a first graph pattern having a first axis along which time is plotted and a second axis along which measured systolic and diastolic blood pressures are plotted;

reading means for reading the times and the information out of said memory means in a time series;

blood pressure developing means for developing the systolic and diastolic blood pressure values from the information read out by said reading means as positions on the first graph patern using the times clocked by said timekeeping means;

line segment developing means for developing line segments connecting the systolic and diastolic blood pressure values developed by said blood pressure developing means at each of the times clocked by said tiemkeeping means, the line segments forming a bar graph pattern;

second pattern holding means for holding a second graph pattern having a first axis along which systolic blood pressure is plotted and a second axis along which diastolic blood pressure is plotted including a reference blood pressure pattern for blood pressure diagnosis superposed on the first and second graph axes;

calculating means for calculating based on the systolic and diastlic blood pressure values measured by said measuring means, a point of intersection indicating the systolic and diastolic blood pressure values on the second graph pattern held by said second pattern holding means;

intersection developing means for developing the point of intersection calculated by said calculating means as data on the second graph pattern;

printing means for recording on recording media the bar graph pattern developed by said line segment developing means in the first function mode and, in the second function mode, the second graph pattern and the data developed by said intersection developing means; and control means for controlling transmission of the blood pressure values and the bar graph pattern developed by said blood pressure developing means and said line segment developing means, respectively, in the first function mode and, in the second function mode, controlling transmission of the second graph pattern and the data developed by said intersection developing means to said printing means, whereby in the first functon mode, the systolic and diastolic blood pressure values and the bar graph pattern are indicated and recorded on the recording media and in the second function mode, the systolic and diastolic blood pressure values are indicated and recorded on the recording media as the point of intersection on the second graph pattern and the reference blood pressure pattern is indicated and recorded in a form superposed on the point of intersection in the second graph pattern.

8. An electronic sphygmomanometer according to claim 7, wherein the reference blood pressure pattern held in said second pattern holding means includes a safe area, a questionable area and a danger area of systolic and diastollic blood pressure and said printing means records the safe area, the questionable area and the danger area superposed on the point of intersection under the control of said control means in the second function mode.

9. An electronic sphygmomanometer comprising:
measuring means for measuring information related to blood pressure at a plurality of times, the information including at least systolic and diastolic blood pressure values;

pattern holding means for holding a graph pattern having a first axis along which systolic blood pressure is plotted and a second axis along which diastolic blood pressure is plotted;

reference region developing means for developing reference data including a safe area, a questionable area and a danger area of systolic and diastolic blood pressure values;

calculating means for calculating, based on the systolic and diastolic blood pressure values measured by said measuring means, a point of intersection indicating the systolic and diastolic blood pressure values on the graph pattern held by said pattern holding means;

intersection developing means for developing the point of intersection calculated by said calculating means as intersection data on the graph pattern;

recording means for recording the safe area, the questionable area and the danger area of the systolic and diatolic values onto recording media to form a graph with axes corresponding to systolic and diastolic blood pressure;

printing means for recording on the recording media, the graph pattern and the reference and intersection data resulting from the developing performed by said reference region and intersection developing means; and control means for controlling transmission of the graph pattern from said pattern holding means and the reference region and intersection data developed by said reference region and intersection developing means to said printing means, whereby the systolic and diastolic blood pressure values are indicated and recorded as the point of intersection on the graph pattern and the safe area, questionable area and danger area of systolic and diasatolic blood pressure are indicated and recorded in a form superposed on the point of intersection.

10. A method for automatically displaying blood pressure in a graphical format, comprising the steps of:
(a) sphygmomanometrically measuring blood pressure at a plurality of times to produce information related thereto, the information including at least systolic and diastolic blood pressure values;
(b) storing the information measured in step (a);
(c) storing a graph pattern having a first axis along which systolic blood pressure is plotted and a second axis along which diastolic blood pressure is plotted, a reference blood pressure region for blood pressure diagnosis being included in the graph pattern;

(d) calcualting a point of intersection corresponding to the systolic and diastolic blood pressure values measured in step (a) with reference to the graph pattern stored in step (c); and
(e) recording on recording media the graph pattern including the reference blood pressure region for blood pressure diagnosis superposed on the point of intersection calculated in step (d).

* * * * *

UNITED STATES PATENT AND TRADEMARK OFFICE
CERTIFICATE OF CORRECTION

PATENT NO. : 4,747,412

DATED : May 31, 1988

INVENTOR(S) : Yamaguchi

It is certified that error appears in the above-identified patent and that said Letters Patent is hereby corrected as shown below: On the title page:

Front page [56] References Cited, line 4, "6/1981" should be --10/80--;

line 6, "Bilgutoy" should be --Bilgutay--;

line 14, "Concurrently" should be --Concurrent--;

line 16, "13" should be --31--.

Front page, Col. 2, line 3, "Hodley" should be --Hadley--;

line 4, "Am" should be --Ann--.

Col. 4, line 11, "provided" should be --providing--.

Col. 6, line 8, "19-5" should be --19-25--.

UNITED STATES PATENT AND TRADEMARK OFFICE
CERTIFICATE OF CORRECTION

PATENT NO. : 4,747,412

DATED : May 31, 1988

INVENTOR(S) : Yamaguchi

It is certified that error appears in the above-identified patent and that said Letters Patent is hereby corrected as shown below:

Col. 8, line 54, after "thirty" insert --times--.

Col. 9, line 13, "segement" should be --segment--;

line 22, "stared.)" should be --stored.)--.

Col. 12, line 27, "print-cut," should be --print-out,--.

Col. 14, line 37, "elelctronic" should be --electronic--;

line 58, "5" should be --5,--.

Col. 15, line 22, "patern" should be --pattern--;

line 37, "calculating" (2nd occurrence) should be --calculating,--;

line 38, "diastlic" should be --diastolic--.

Col. 17, line 1, "calcualting" should be --calculating--.

Signed and Sealed this

Eighth Day of November, 1988

Attest:

DONALD J. QUIGG

Attesting Officer

Commissioner of Patents and Trademarks